United States Patent
Orban, III (10) Patent No.: US 7,666,197 B2
(45) Date of Patent: Feb. 23, 2010

(54) METHOD AND APPARATUS FOR ANASTOMOSIS

(75) Inventor: Joseph P. Orban, III, Norwalk, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 798 days.

(21) Appl. No.: 10/516,434

(22) PCT Filed: Jun. 19, 2003

(86) PCT No.: PCT/US03/19516

§ 371 (c)(1),
(2), (4) Date: Nov. 30, 2004

(87) PCT Pub. No.: WO04/000138

PCT Pub. Date: Dec. 31, 2003

(65) Prior Publication Data

US 2005/0251155 A1  Nov. 10, 2005

Related U.S. Application Data

(60) Provisional application No. 60/390,106, filed on Jun. 19, 2002.

(51) Int. Cl.
A61B 17/08 (2006.01)
A61B 17/10 (2006.01)

(52) U.S. Cl. .................................. 606/153; 606/139
(58) Field of Classification Search ............... 606/153, 606/154, 155, 156, 157, 158, 139
See application file for complete search history.

(56) References Cited

U.S. PATENT DOCUMENTS 5,591,206 A * 1/1997 Moufarrege ................ 606/215
5,817,108 A * 10/1998 Poncet ........................ 606/139
6,051,007 A * 4/2000 Hogendijk et al. .......... 606/151

* cited by examiner

Primary Examiner—Vy Q Bui (57) ABSTRACT

Apparatus and methods for performing a surgical anastomotic procedure are disclosed herein. Apparatus according to the present disclosure include at least one fastener including a first fastener portion having an anchoring leg portion, a second fastener portion including an anchoring leg portion, wherein the first and second fastener portions are operatively associated with one another to selectively fix the position of the first fastener portion relative to the second fastener portion. The apparatus has a first member for engaging the first fastener portion and a second member for engaging the second fastener portion. The first member and the second member are movable with respect to one another to move the first fastener portion and second fastener portion with respect to one another.

13 Claims, 6 Drawing Sheets

FIG. 13B

METHOD AND APPARATUS FOR ANASTOMOSIS

CROSS REFERENCE TO RELATED APPLICATIONS

This is a National Stage Application of PCT/US 03/19516 under 35 USC §371(a), which claims priority of U.S. Provisional Patent Application Ser. No. 60/390,106 filed Jun. 19, 2002, now abandoned, the entire contents of which are hereby incorporated by reference.

BACKGROUND

1. Technical Field

The present disclosure relates to apparatus and methods used for joining tissue portions and more particularly, to anastomotic devices and methods for positioning and joining two hollow body parts.

2. Background of Related Art

Anastomosis is the bringing together and/or joining of two hollow or tubular structures. When it is desired to suture a body conduit, typically for attachment to another body conduit, sutures are placed around the circumference of the conduit in order to maintain the patency of its lumen or channel. It can be appreciated that the sutures made on top of the conduit (i.e., on the side facing the surgeon) are made relatively more easily than the sutures made underneath the conduit (i.e., on the side facing away from the surgeon).

The complexity of joining two body vessels is made manifestly apparent in a surgical procedure referred to generally as a radical prostatectomy (i.e., a well established surgical procedure for patients with localized prostatic carcinoma). In general, radical prostatectomy procedures require the removal of cancerous tissue while preserving sexual function and continence in the patient. There are two primary types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, i.e., next to the external urethral sphincter. Next, the prostatic urethra is divided, the prostatic urethra and the prostate gland through which it goes are then pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder, will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and positioned against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult and complex. This difficulty is complicated by the tendency of the urethral stump to retract into adjacent tissue. As a result, considerable time and effort must be expended to re-expose the urethral stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179, issued to Edelstein, there is disclosed a suturing device including a shaft with portions defining an interior channel extending between a proximal and a distal end of the shaft. This channel includes a generally axial lumen which extends to the proximal end of the shaft and a generally transverse lumen which extends from the axial lumen distally outwardly to an exit hole at the outer surface of the shaft. A needle and suture can be back loaded to the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164, issued to Roth, there is disclosed a suture guide with a curved distal portion. The distal portion of the suture guide has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039, issued to Avant et al., there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stump to the bladder neck easier. As such, each surgical procedure using prior art devices continues to be time consuming and requires great skill in order to be performed. Accordingly, the need exists for anastomosis devices which overcome the drawbacks of the prior art devices and which are quick and simple to use.

SUMMARY

Apparatus and methods for performing a surgical anastomotic procedure are disclosed herein. According to one aspect of the present disclosure, an apparatus for approximating body vessels includes at least one fastener. Each fastener includes a first fastener portion having an anchoring leg portion, and a second fastener portion having an anchoring leg portion, wherein the first and second fastener portions are operatively associated with one another for selectively fixing the position of the first fastener portion and the second fastener portion with respect to one another. The apparatus further includes a first member configured and adapted to engage the first fastener portion, and a second member configured and adapted to engage the second fastener portion, the first member and the second member being movable with respect one another to move the first fastener portion and second fastener portion with respect to one another.

It is envisioned that each first fastener portion and second fastener portion has a locking leg portion and a first position in which the anchoring leg portion is adjacent the locking leg portion and a second position in which the anchoring leg portion is spaced a distance from the locking leg portion.

Each of the anchoring leg portions of the first and second fastener portions can include a sharpened tip, wherein the sharpened tips are oriented substantially toward one another. Each anchoring leg portion can be integrally connected to the respective locking leg portion.

In certain embodiments, the apparatus further includes an insertion sleeve. Accordingly, it is envisioned that each anchoring leg portion can be biased to a position spaced from the respective locking leg portion and collapsible to a position in close proximity to the respective locking leg portion.

It is envisioned that each fastener can be made from stainless steel, titanium, polyglycolic acid and polylactic acid.

In certain embodiments, the first fastener portion and the second fastener portion include inter-engaging fixing elements. The fixing elements can include a series of projections formed along a surface of the first fastener portion, and a locking passage formed along a surface of the second fastener portion, the locking passage being configured and dimensioned to receive an end of the first fastener portion therein. The locking passage can include at least one projection extending from an inner surface thereof and the at least one projection is configured and dimensioned to engage the series of projections formed along the surface of the first fastener portion. Desirably, the fixing elements are saw toothed. Accordingly, the fixing elements permit movement of the first fastener portion relative to the second fastener portion in a first direction, while preventing movement in a second direction.

It is envisioned that each of the first fastener portion and the second fastener portion can have a locking leg portion pivotably connected to the respective anchoring leg portion.

Each anchoring leg portion can include a suture secured thereto.

In certain embodiments, the apparatus can further include an insertion sleeve. It is envisioned that a plurality of fasteners can be radially disposed about the lumen of the insertion sleeve.

It is envisioned that each first fastener portion can include a lip extending from the first fastener portion and the first member can include an anvil having a hook formed at a distal end thereof for engaging the lip of the first fastener portion. It is further envisioned that each second fastener portion can include a lip extending from the second fastener portion and the second member can include a pusher having a recess formed in a distal end thereof for engaging the lip of the second fastener portion.

In certain embodiments, the apparatus can further include fixing elements on each of the first and second fastener portions. The fixing elements can include a series of projections formed along a surface of the first fastener portion, and a locking passage formed along a surface of the second fastener portion, the locking passage being configured and dimensioned to receive an end of the locking leg portion of the first fastener portion therein. The locking passage includes at least one projection extending from an inner surface thereof which at least one projection is configured and dimensioned to engage the series of projections formed along the surface of the first fastener portion. The locking passage is defined by a pair of side walls extending from the locking leg portion of the second fastener portion and an end wall interconnecting and extending between the pair of side walls, the at least one projection of the locking passage being formed on an inner surface of the end wall.

According to another aspect of the present disclosure, a method of approximating a first body vessel and a second body vessel is provided. The method includes the step of providing an apparatus for approximating the first body vessel and the second body vessel. The apparatus includes at least one fastener having a first fastener portion having an anchoring leg portion, and a second fastener portion having an anchoring leg portion, wherein the first and second fastener portions are operatively associated with one another for selectively fixing the position of the first fastener portion and the second fastener portion with respect to one another, a first member configured and adapted to engage the first fastener portion, and a second member configured and adapted to engage the second fastener portion, the first member and the second member being movable with respect to one another to move the first fastener portion and second fastener portion with respect to one another.

The method further includes the steps of passing the apparatus through the first body vessel and through an opening in the second body vessel such that the anchoring leg portion of the first fastener portion is positioned within the second body vessel, withdrawing the first member to drive the anchoring leg portion of the first fastener portion into the wall of second body vessel, advancing the second member to drive the anchoring leg portion of the second fastener portion into the wall of the first body vessel, and approximating the first member and the second member to approximate the anchoring leg portions of the first and second fastener portions with one another and to approximate the first and second body vessels with one another, wherein the fixing elements engage one another and inhibit separation of the first and second body vessels from one another.

It is envisioned that the anchoring leg portions can be biased to an expanded position and the fastener can be disposed within an insertion sleeve so as to maintain the fastener in a collapsed position. The method can further include the step of withdrawing the insertion sleeve so as to allow the anchoring leg portion to expand.

These and other features of the apparatus disclosed herein, will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and together with the detailed description of the embodiments given below, serve to explain the principles of the present disclosure.

DETAILED DESCRIPTION OF PREFERRED EMBODIMENTS

Preferred embodiments of the presently disclosed anastomosis apparatus will now be described in detail with reference to the drawing figures wherein like reference numerals identify similar or identical elements. In the drawings and in the description which follows, the term "proximal", as is traditional, will refer to the end of the surgical device or instrument of the present disclosure which is closest to the operator, while the term "distal" will refer to the end of the device or instrument which is furthest from the operator.

An anastomosis apparatus 100, in accordance with an embodiment of the present disclosure, is shown in FIGS. 1-12. Although anastomosis apparatus 100 offers significant advantages to a radical prostatectomy procedure, it will be understood that the device is applicable for use in any anastomotic procedure where two body vessels are to be brought together and joined.

Figure 5:
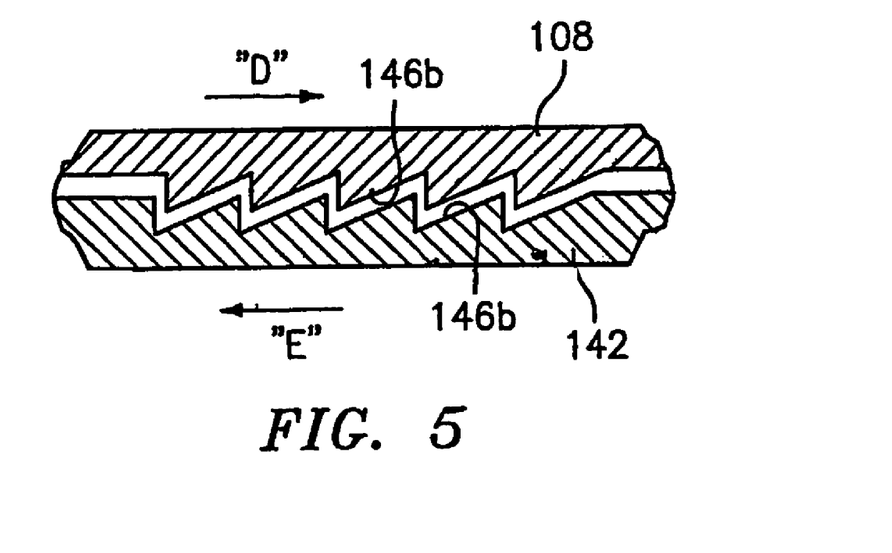
FIG. 5 is an enlarged cross-sectional view of the indicated area of FIG. 3.
Figure 6:
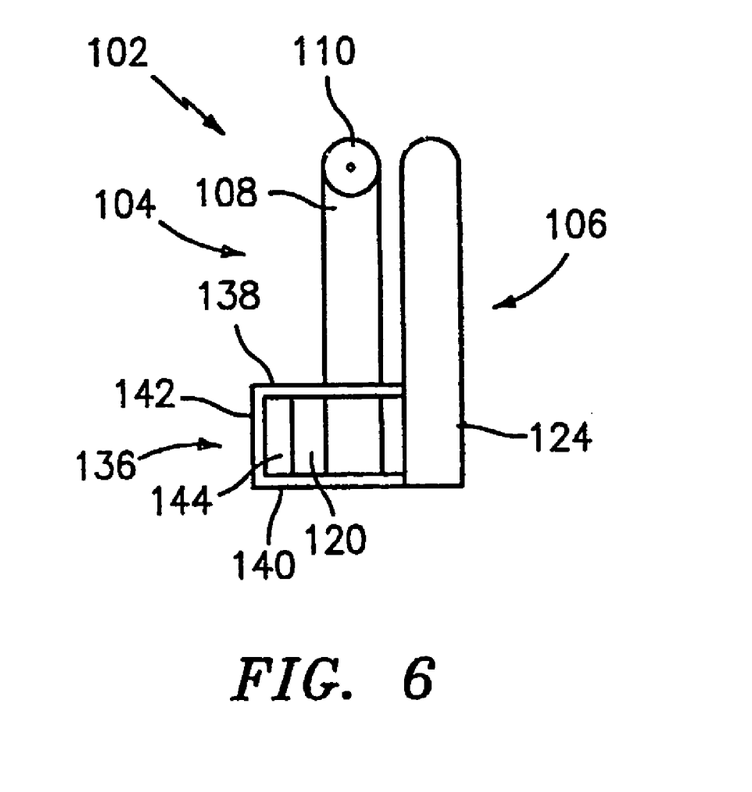
FIG. 6 is an enlarged end view of the fastener of FIGS. 1-5.
Figure 7:
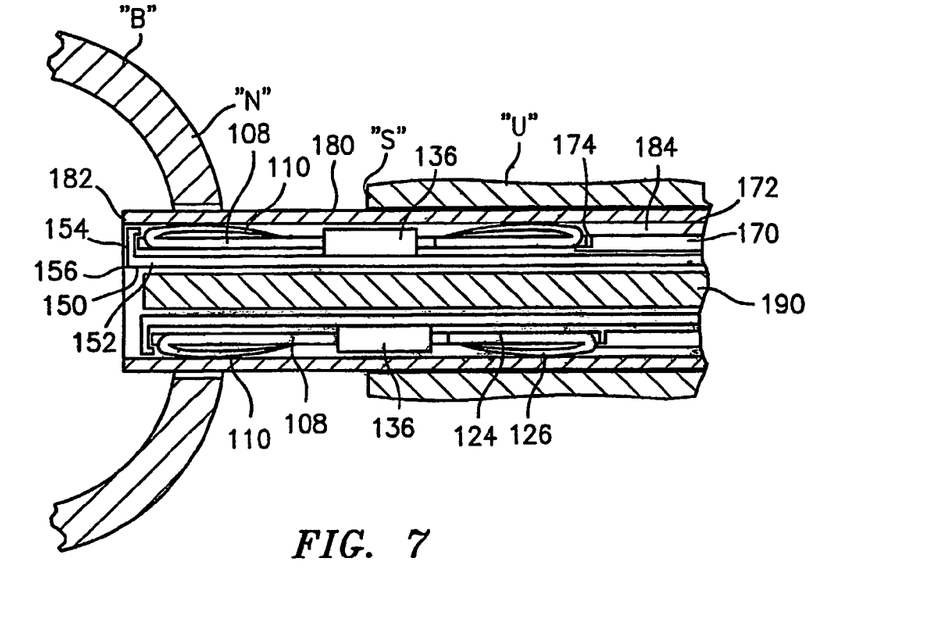
FIG. 7 is a cross-sectional side elevational view illustrating the positioning of the insertion tool and fastener into a hollow body organ.
Figure 8:
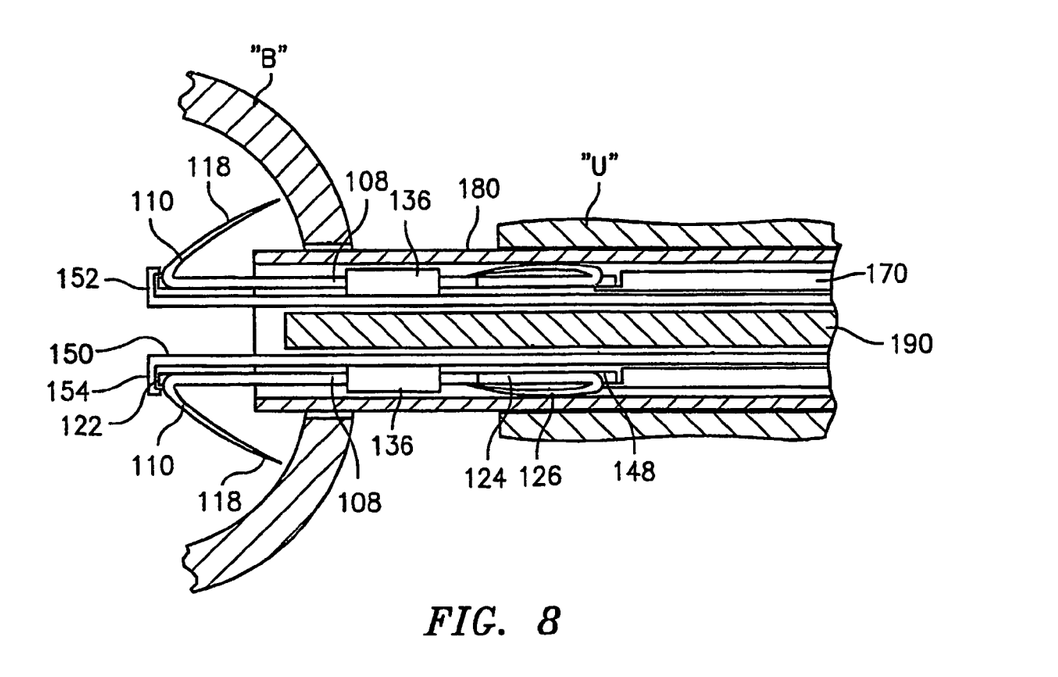
FIG. 8 is a cross-sectional side elevational view illustrating the positioning of the insertion tool and the fastener as well as the expansion of the distal of the fastener in the hollow body organ in order to anchor the distal end of the fastener in the walls of the hollow body organ.

As seen in FIGS. 1-6, anastomosis apparatus 100 includes at least one fastener 102 and preferably a plurality of fasteners 102 radially disposed about a lumen 184 of an insertion sleeve 180 (see FIG. 7). Each fastener 102 includes a first fastener portion 104 and a second fastener portion 106. First fastener portion 104 of fastener 102 includes a locking leg portion 108 and an anchoring leg portion 110 integrally formed with locking leg portion 108. In particular, locking leg portion 108 includes a proximal end 112 and a distal end 114 from which anchoring leg portion 110 extends. Anchoring leg portion 110 includes a distal end 116 integrally coupled to distal end 114 of locking leg portion 108 and a sharpened proximal tip 118. Desirably, sharpened proximal tip 118 of anchoring leg portion 110 is oriented towards proximal end 112 of locking leg portion 108. Anchoring leg portion 110 has a first position "A" in which sharpened proximal tip 118 is spaced a distance from locking leg portion 108 and can be collapsed to a second position "C" (as seen in phantom in FIGS. 2 and 3) in which sharpened proximal tip 118 is in close proximity to locking leg portion 108.

Figure 1:
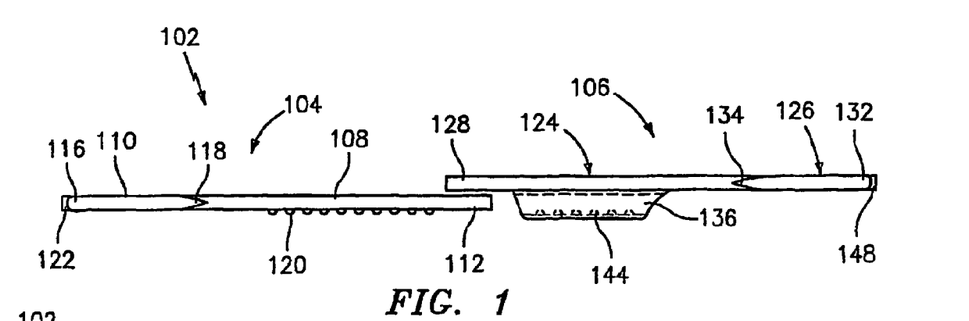
FIG. 1 is a top plan view of a fastener, in accordance with an embodiment of the present disclosure, shown in a separated condition.
Figure 2:
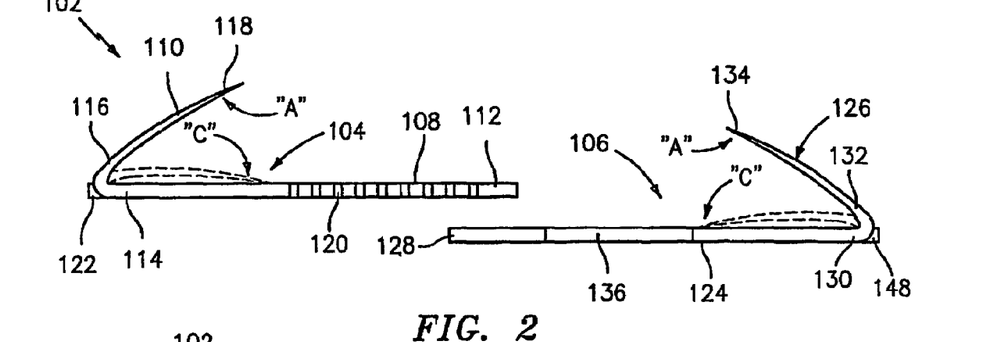
FIG. 2 is a side elevational view of the fastener of FIG. 1.
Figure 3:
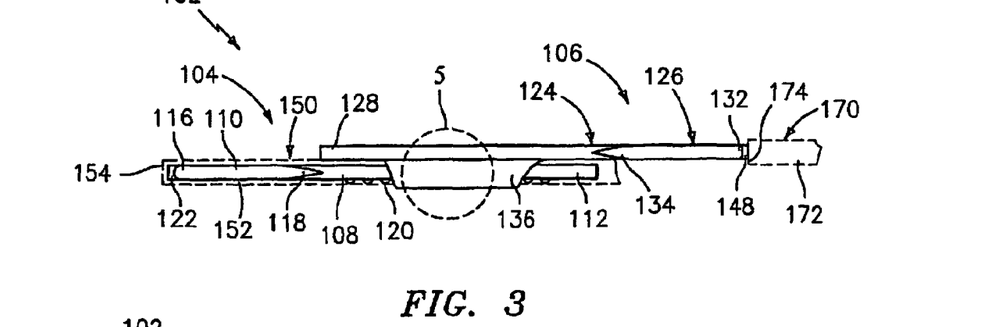
FIG. 3 is a top plan view the fastener of FIGS. 1-2, shown in a coupled condition.
Figure 4:
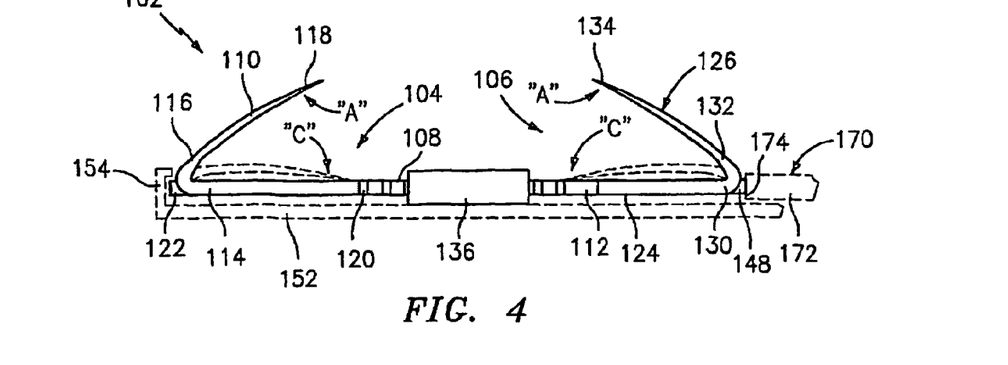
FIG. 4 is a side elevational view of the fastener of FIGS. 1-3.

Preferably, locking leg portion 108 of first fastener portion 104 includes fixing elements for engaging second fastener portion 106. The fixing elements in certain embodiments comprise a series of projections 120 formed along a side thereof and extending from proximal end 112 toward distal end 114. First fastener portion 104 of fastener 102 further preferably includes a lip 122 projecting distally from distal end 110 of locking leg portion 108.

Second fastener portion 106 of fasteners 102 includes a locking leg portion 124 and an anchoring leg portion 126 integrally formed with locking leg portion 124. In particular, locking leg portion 124 includes a distal end 128 and a proximal end 130 from which anchoring leg portion 126 extends. Anchoring leg portion 126 includes a proximal end 132 integrally coupled to proximal end 130 of locking leg portion 124 and a sharpened distal tip 134. Desirably, sharpened distal tip 134 of anchoring leg portion 126 is oriented towards distal end 128 of locking leg portion 124. Anchoring leg portion 126 has a first position "A" in which sharpened distal tip 134 is spaced a distance from distal end 128 of locking leg portion 124 and can be collapsed to a second position "C" (as seen in phantom in FIGS. 2 and 4) in which sharpened distal tip 134 is in close proximity to locking leg portion 124.

Preferably, locking leg portion 124 of second fastener portion 106 includes a locking passage 136 formed along a side surface thereof. As seen in FIG. 6, locking passage 136 is defined by an upper wall 138 extending from an upper surface of locking leg portion 124, a lower wall 140 extending from a lower surface of locking leg portion 124 and an interconnecting side wall 142 extending between the terminal ends of upper wall 138 and lower wall 140. Locking passage 136 includes at least one, and desirably a plurality of fixing elements for engaging the fixing elements of the first fastener portion 104. The locking passage 136 shown has fixing elements in the form of a plurality of projections 144 formed along an inner surface of interconnecting side wall 142 and oriented toward locking leg portion 124. Locking passage 136 is sized and dimensioned to slidably receive end of first fastener portion 104 therethough. In particular, when locking leg portion 108 of first fastener portion 104 is inserted into locking passage 136 of second fastener portion 106, projections 120 of locking leg portion 108 engage projections 144 of locking passage 136 to thereby effectively lock first fastener portion 104 of fastener 102 in position with respect to second fastener portion 106 of fastener 102.

Similar to first fastener portion 104 of fastener 102, second fastener portion 106 of fastener 102 includes a lip 148 projecting proximally from proximal end 130 of locking leg portion 124.

As seen in FIG. 5, it is contemplated that projections 120 of locking leg portion 108 and projections 144 of side wall 142 of locking passage 136 are teeth-like (e.g., saw toothed) projections 146a, 146b, respectively, configured and adapted to permit locking leg portion 108 to be inserted into locking passage 136 and hindering withdrawal of locking leg portion 108 therefrom. In particular, projections 146a, 146b are configured and adapted to permit locking leg portion 108 to slide in direction "D" while locking passage 136 is permitted to slide in direction "E". However, once projections 146a and projections 146b engage one another, projections 146a, 146b prevent locking leg portion 108 from sliding in a direction opposite to direction "D" and prevent locking passage 136 from sliding in the direction opposite from "E". In other words, projections 146a, 146b are configured and adapted to allow uni-directional movement of locking leg portion 108 relative to locking passage 136 and in turn unidirectional movement of first fastener portion 104 relative to second fastener portion 106.

While projections 120 of locking leg portion 108 and locking passage 136 are shown and described as being formed along a side surface of first fastener portion 104 and second fastener portion 106, respectively, it is envisioned and within the scope of the present disclosure that projections 120 can be provided along any surface of locking leg portion 108 of first fastener portion 104 and locking passage 136 can be provided along any surface of locking leg portion 124 of second fastener portion 106.

First fastener portion 104 and second fastener portion 106 of fastener 102 can be made from any surgical grade material, such as stainless steel or titanium. It is envisioned that first and second fastener portions 104, 106 are preferably made from a medical grade bio-absorbable material, such as, for example, polyglycolic acid (PGA) and/or polylactic acid (PLA). Preferably, the material and dimensions of fasteners 102 are selected such that fasteners 102 will dissolve after a predetermined period of time while retaining their structural integrity for a period of time sufficient to assure proper healing of the anastomosis site.

As seen in phantom in FIG. 7, anastomosis apparatus 100 includes a first member or anvil 150, a second member or pusher 170, and a shaft 190 for mounting the fasteners 102 in an insertion sleeve 180. The anvil 150 and pusher 170 are shown in phantom in FIGS. 3 and 4. Anvil 150 includes an elongate body portion 152 and a hook 154 formed at a distal end 156 thereof. Hook 154 of anvil 150 is configured and adapted to engage lip 120 of first fastener portion 104 of fastener 102. Pusher 170 includes an elongate body portion 172 and a recess 174 formed at a distal end 176 thereof. Recess 174 of pusher 170 is configured and adapted to engage lip 146 of second fastener portion 106 of fastener 102.

As seen in FIGS. 7-11, insertion sleeve 180 includes a distal end 182, a proximal end (not shown) and defines a lumen 184 extending therethrough which defines a central axis. Shaft 190 is configured and adapted to be slidably received in lumen 184 of insertion sleeve 180. It is envisioned that shaft 190 include a plurality of radially oriented longitudinally extending grooves (not shown) formed therein. Accordingly, each groove of shaft 190 can be configured and adapted to receive a respective anvil 150, pusher 170 and fastener 102. Preferably, shaft 190 is sized such that when shaft 190 is inserted into sleeve 180, anchoring leg portion 108 of first fastener portion 104 and anchoring leg portion 124 of second fastener portion 106 are in the second position "C" (see FIG. 7).

Anvil 150 and pusher 170 are arranged with respect to one another so as to form a recess for receiving fastener 102 between hook 154 and recess 174. Fastener 102 is disposed in the recess so that first fastener portion 104 and second fastener portion 106 are engaged with one another, leaving room for advancing the anchoring leg portions toward one another. A plurality of fasteners 102 are disposed in insertion sleeve 180, with the shaft 190 disposed between the fasteners 102 and their corresponding anvil and pusher. (see FIG. 7).

A preferred method of use and operation of anastomosis apparatus 100 in performing a radical prostatectomy anastomosis will now be described in greater detail with reference to FIGS. 1-12 and in particular with reference to FIGS. 7-12. Anastomosis apparatus 100 can be used in either the retropubic or the perineal prostatectomy approaches, or any approach in which the bladder and urethra must be approximated. With the prostate removed, the bladder neck "N" of the bladder "B" is first reconstructed by everting the inner mucosal lining of bladder "B" and suturing it down to the outer wall of bladder "B", using known surgical techniques. Likewise, urethral stump "S" of urethra "U" is reconstructed by everting the inner mucosal lining of urethral stump "S" and suturing it down to the outer wall of urethra "U", using known surgical techniques.

Preferably, with bladder neck "N" reconstructed, bladder neck "N" is sized to properly accommodate and retain distal end 180 of sleeve 180 within bladder "B" using a standard tennis racket type closure (i.e., the opening of the bladder neck constituting the head of the tennis racket and a radial incision extending from the bladder neck constituting the handle portion of the tennis racket). The size of the bladder neck will vary depending on the patient. Typically, the bladder neck "N" is sized to be approximately 7-8 mm in diameter.

With bladder neck "N" reconstructed, apparatus 100 is passed trans-urethrally through urethra "U" until distal end 182 of insertion sleeve 180 extends out of urethral stump "S" and into bladder "B" through bladder neck "N", as seen in FIG. 7.

With apparatus 100 so positioned, insertion sleeve 180 is withdrawn in a proximal direction to expose sharpened proximal tips 118 of first fastener portions 104. The anchoring leg portions 110 are biased to the first position "A" so that when sharpened proximal tips 118 are exposed from within insertion sleeve 180, anchoring leg portions 110 of first fastener portions 104 are deployed to the first position "A". (see FIG. 8). With anchoring leg portions 110 deployed, hooks 154 of anvils 150 are withdrawn in a proximal direction to engage lips 122 of first fastener portions 104 and to drive sharpened proximal tips 118 through the wall of bladder "B", see FIG. 9.

Figure 9:
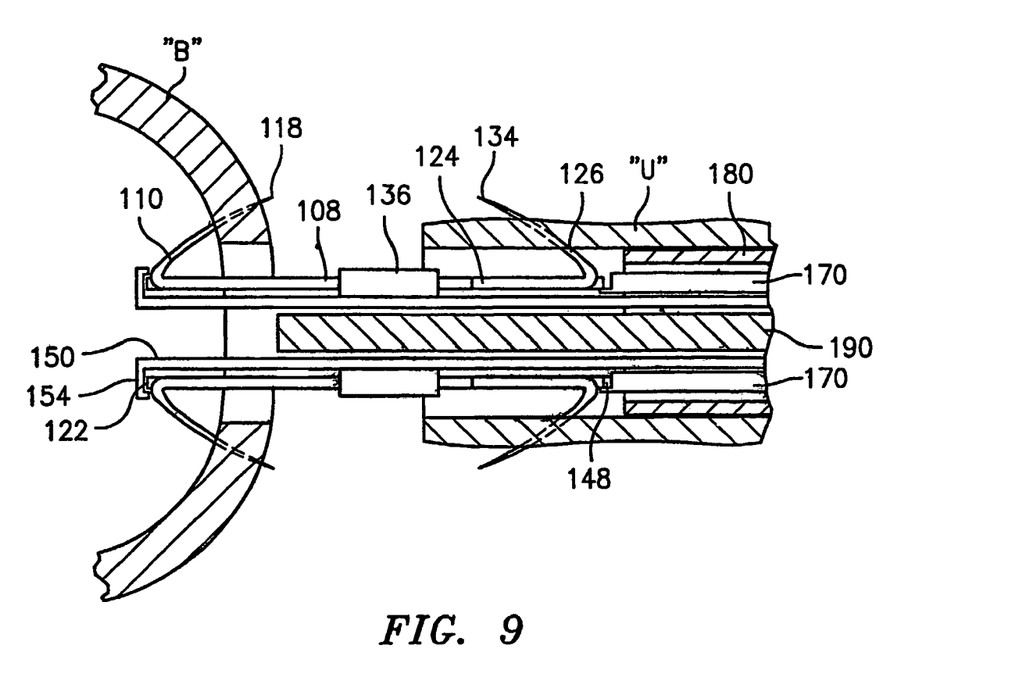
FIG. 9 is a cross-sectional side elevational view illustrating the expansion of the proximal end of the fastener in order to anchor the proximal end of the fastener to the walls of the body lumen.
Figure 10:
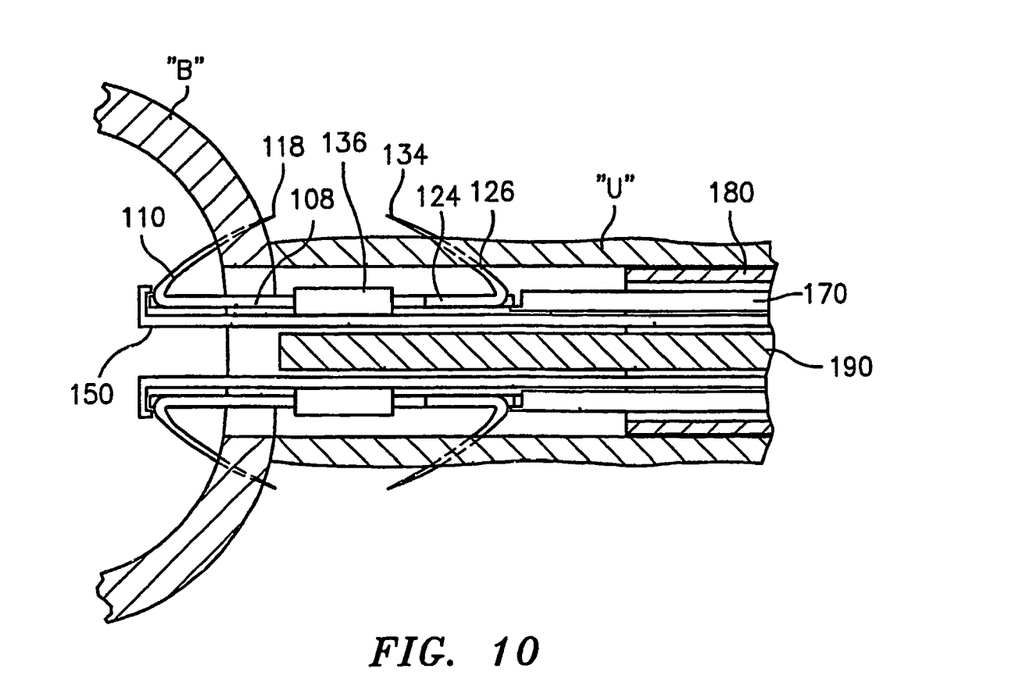
FIG. 10 is a cross-sectional side elevational view illustrating the approximation of the hollow body organ to the body lumen.
Figure 11:
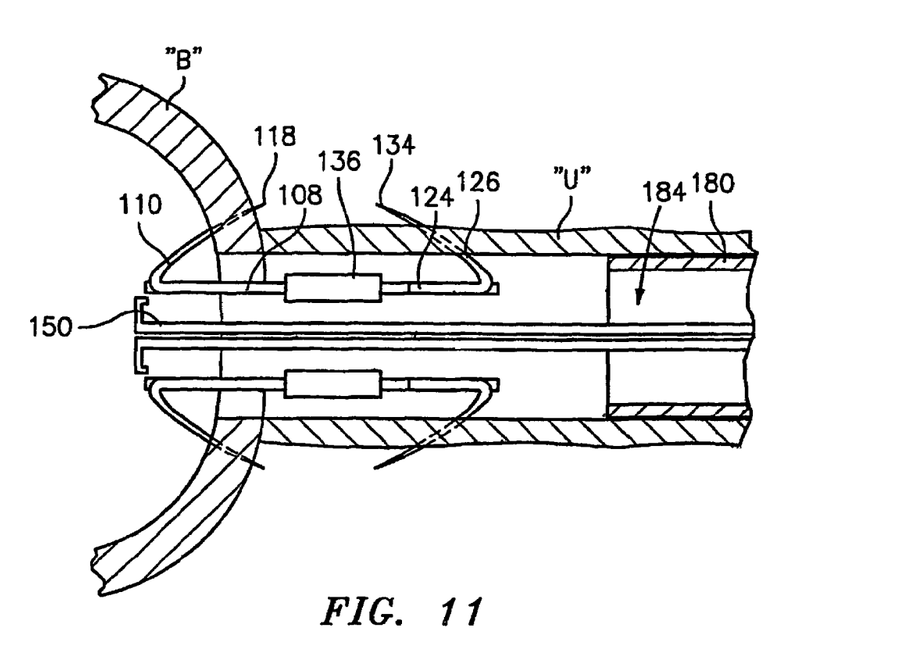
FIG. 11 is a cross-sectional side elevational view illustrating the retraction of the insertion tool.
Figure 12:
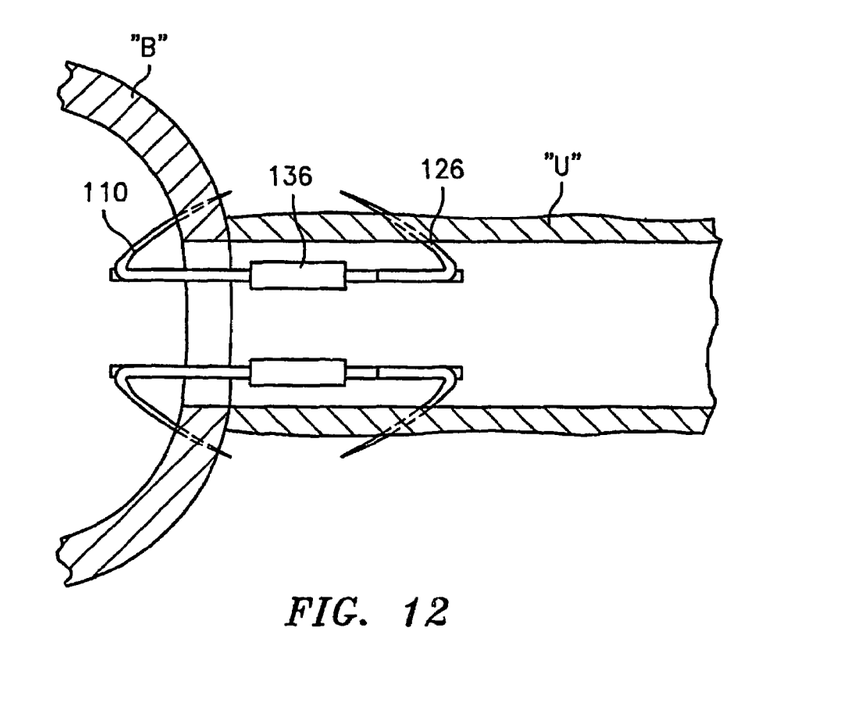
FIG. 12 is a cross-sectional side elevational view illustrating the final anastomosed hollow body organ and body lumen with the fastener anchored in position.

As seen in FIG. 9, insertion sleeve 180 is further withdrawn in a proximal direction until sharpened distal tips 134 and anchoring leg portion 126 of second fastener portion 106 are exposed. The anchoring leg portions 126 are biased to the first position "A" so that when anchoring leg portions 126 are completely exposed from within insertion sleeve 180, anchoring leg portions 126 of second fastener portions 106 are deployed to first position "A". (see FIG. 9). With anchoring leg portions 126 deployed, pushers 170 are advanced in, a distal direction to engage lips 148 and to drive sharpened distal tips 134 through the wall of urethral stump "S".

With sharpened proximal tips 118 of first fastener portions 104 penetrating the wall of bladder "B" and with sharpened distal tips 134 penetrating the wall of urethral stump "S", hooks 154 of anvils 150 are approximated toward recesses 174 of pushers 170 to thereby approximate anchoring leg portions 110 of first fastener portion 104 and anchoring leg portions 126 of second fastener portion 106 towards one another. Concomitantly, as anchor leg portions 110 and 126 are approximated towards one another bladder neck "N" is approximated towards urethral stump "S". (see FIG. 10). In accordance with the present disclosure, approximation of anchor legs 110 and 126 towards one another results in projections 120 and 144 incrementally engaging one another and maintaining the position of anchor leg 110 relative to anchor leg 126. Accordingly, projections 120 and 144 prevent bladder "B" from separating from urethra "U".

After bladder neck "N" has been approximated toward urethral stump "S", pushers 170 and shaft 190 are withdrawn from insertion sleeve 180 and anvils 150 unhooked from lips 122. (see FIG. 11). Thereafter, anvils 150 and insertion sleeve 180 are withdrawn from urethra "U".

Figure 13A:
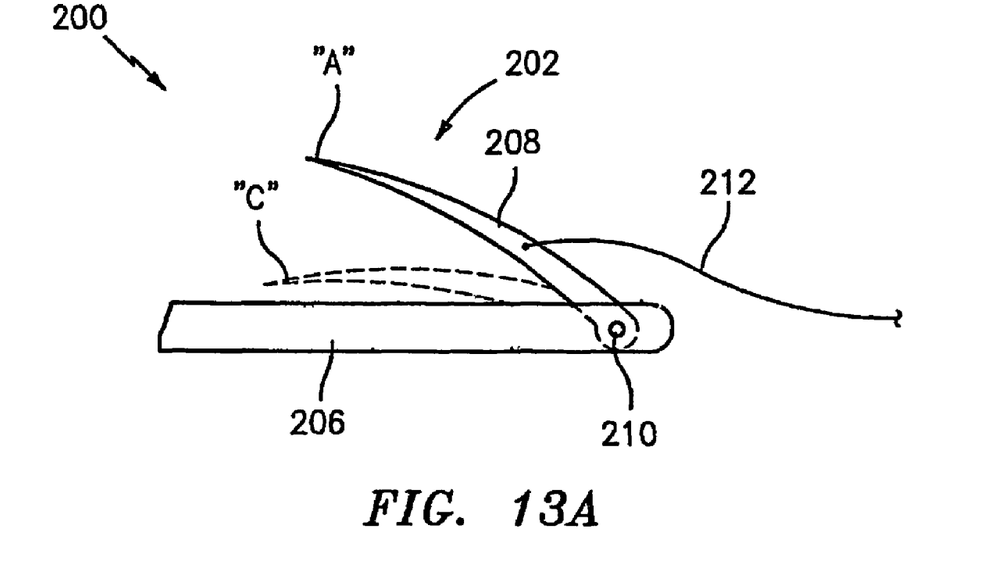
FIG. 13A is a side elevational view of a proximal leg of a fastener in accordance with an alternative embodiment of the present disclosure.
Figure 13B:
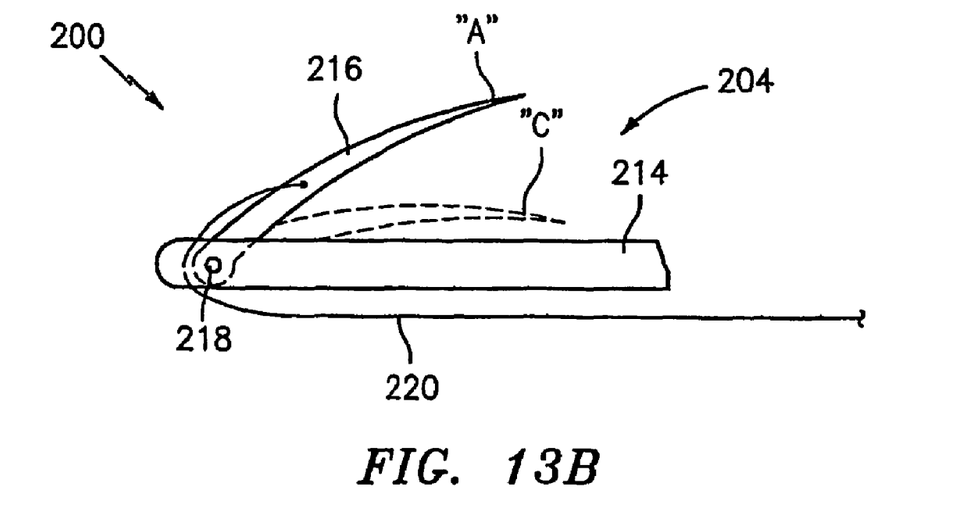
FIG. 13B is a side elevational view of a distal leg of a fastener in accordance with the alternative embodiment of the present disclosure.

An alternate embodiment of a fastener 200, in accordance with the present disclosure, is shown in FIGS. 13A and 13B. Unlike fastener 102 from above, fastener 200 includes a first fastener portion 202 and a second fastener portion 204. First fastener portion 202 includes a locking leg portion 206 and an anchoring leg portion 208 pivotally coupled to a proximal end of locking leg portion 206. In the embodiment shown, anchoring leg portion 208 is pivotally coupled to locking leg portion 206 by a pivot pin 210, but other means known in the art may also be used. Alternatively, locking leg portion 206 or anchoring leg portion 208 can be provided with an integrally formed pin that extends outwardly for receipt in an aperture formed in the other of locking leg portion 206 or anchoring leg portion 208. First fastener portion 202 includes a suture 212 connected to anchoring leg portion 208 for pulling on anchoring leg portion 208 and lifting a distal end of anchoring leg portion 208 away from locking leg portion 206 (e.g., from first position "A" to second position "C"). It is contemplated that the proximal end of locking leg portion 206 includes a stop (not shown) for stopping the lifting of anchoring leg portion 208 beyond a predetermined amount.

As seen in FIG. 13B, second fastener portion 204 includes a locking leg portion 214 and an anchoring leg portion 216 pivotally coupled to a distal end of locking leg portion 214 by a pivot pin 218. Alternatively, locking leg portion 214 or anchoring leg portion 216 can be provided with an integrally formed pin and extending outwardly for receipt in an aperture formed in the other of locking leg portion 214 or anchoring leg portion 216. Second fastener portion 204 further includes a suture 220 connected to anchoring leg portion 216, extending around the distal end of locking leg portion 214, for pulling on anchoring leg portion 216 and lifting a proximal end of anchoring leg portion 216 away from locking leg portion 214 (e.g., from first position "A" to second position "C"). It is contemplated that the distal end of locking leg portion 214 includes a stop (not shown) for stopping the lifting of anchoring leg portion 216 beyond a predetermined amount.

While apparatus in accordance with the present disclosure have been described as being used in connection with a radical prostatectomy procedure, it is envisioned that apparatus having similar structures and modes of operation can be used in various other surgical procedures. It will be understood that various modifications may be made to the embodiments of the presently disclosed anastomosis device and method disclosed herein. For example, one or more fasteners may be arranged in the insertion sleeve. In further embodiments, the insertion sleeve is sized to accommodate the fastener without requiring the anchoring leg portions to collapse to position "C". The fastener may comprise a single part with a corrugated, hinged or collapsible portion. The fasteners, in certain embodiments, comprise a fixing element comprising a separate part.

Therefore, the above description should not be construed as limiting, but merely as an exemplification of a preferred embodiment. Those skilled in the art will envision other modifications within the scope of the present disclosure.

The invention claimed is:

1. An apparatus for approximating body vessels, comprising:
   at least one fastener including:
      a first fastener portion having an anchoring leg portion and a locking leg portion;
      a second fastener portion having an anchoring leg portion and a locking leg portion, wherein the first and second fastener portions are operatively associated with one another by an interconnecting feature allowing for selectively fixing the position of the first fastener portion and the second fastener portion with respect to one another; and
      wherein at least one of the first fastener portion and the second fastener portion has a first position in which the anchoring leg portion is adjacent the locking leg portion and a second position in which the anchoring leg portion is spaced a distance from the locking leg portion;
   a suture operably associated with the anchoring leg portion of at least one of the first fastener portion and the second fastener portion wherein the anchoring leg portion of at least one of the first and second fastener portions is repositionable between the first and second positions upon manipulation of the suture;
   a first member configured and adapted to engage the first fastener portion; and
   a second member configured and adapted to engage the second fastener portion, the first member and the second member being movable with respect to one another to move the first fastener portion and second fastener portion with respect to one another.

2. The apparatus according to claim 1, wherein each of the anchoring leg portions of the first and second fastener portions includes a sharpened tip, wherein the sharpened tips are oriented substantially toward one another.

3. The apparatus according to claim 1, wherein each fastener is made from the group of materials consisting of stainless steel, titanium, polyglycolic acid and polylactic acid.

4. The apparatus according to claim 1, further comprising fixing elements on each of the first and second fastener portions.

5. The apparatus according to claim 4, therein the fixing elements include:
   a series projections formed along a surface of the first fastener portion; and
   a locking passage formed along a surface of the second fastener portion, the locking passage being configured and dimensioned to receive an end of the locking leg portion of the first fastener portion therein, wherein the locking passage includes at least one projection extending from an inner surface thereof which at least one projection is configured and dimensioned to engage the series of projections formed along the surface of the first fastener portion.

6. The apparatus according to claim 5, wherein the locking passage is defined by a pair of side walls extending from the locking leg portion of the second fastener portion and an end wall interconnecting and extending between the pair of side walls, the at least one projection of the locking passage being formed on an inner surface of the end wall.

7. The apparatus according to claim 4, wherein the fixing elements permit movement of the first fastener portion relative to the second fastener portion in a first direction and prevent movement in a second direction.

8. The apparatus according to claim 1, wherein the first and second fastener portions have a locking leg portion pivotably connected to the respective anchoring leg portion.

9. The apparatus according to claim 8, wherein each of the first fastener portion and the second fastener portion have a first position in which the anchoring leg portion is adjacent the locking leg portion and a second position in which the anchoring leg portion is spaced a distance from the locking leg portion.

10. The apparatus according to claim 1, wherein the fastener portion includes a lip extending from the first fastener portion, and wherein the first member comprises an anvil having a hook formed at a distal end thereof engaging the lip of the first fastener portion.

11. The apparatus according to claim 10, wherein the second fastener portion includes a lip extending from the second fastener portion, and wherein the second member comprises a pusher having a recess formed in a distal end thereof for engaging the lip of the second fastener portion.

12. An apparatus for approximating body vessels, comprising:
   at least one fastener including:
      a first fastener portion having an anchoring leg portion;
      a second fastener portion having an anchoring leg portion, wherein the first and second fastener portions are operatively associated with one another by an interconnecting feature allowing for selectively fixing the position of the first fastener portion and the second fastener portion with respect to one another; and
   wherein at least one of the anchoring leg portions of the first and second fastener portions includes a sharpened tip configured and dimensioned to penetrate body vessels;
   a suture operably associated with the anchoring leg portion of at least one of the first fastener portion and the second fastener portion wherein the anchoring leg portion of at least one of the first and second fastener portions is repositionable between a first and a second position upon manipulation of the suture;
   a first member configured and adapted to engage the first fastener portion; and
   a second member configured and adapted to engage the second fastener portion, the first member and the second member being movable with respect to one another to move the first fastener portion and second fastener portion with respect to one another.

13. An apparatus according to claim 12, wherein the sharpened tip is configured and dimensioned to anchor the apparatus relative to the body vessel.

* * * * *